United States Patent [19]

Crutchfield

[11] Patent Number: 4,765,325

[45] Date of Patent: Aug. 23, 1988

[54] METHOD AND APPARATUS FOR DETERMINING RESPIRATOR FACE MASK FIT

[76] Inventor: Clifton D. Crutchfield, 7321 N. La Oesta Ave., Tucson, Ariz. 85704

[21] Appl. No.: 940,925

[22] Filed: Dec. 12, 1986

[51] Int. Cl.[4] ............................................ A61M 15/00

[52] U.S. Cl. .......................... 128/202.13; 128/201.23; 128/206.24; 73/40

[58] Field of Search .............................. 73/40, 40.5 R; 128/201.23, 205.25, 206.21, 206.23-206.26, 202.13

[56] References Cited

U.S. PATENT DOCUMENTS

| | | | |
|---|---|---|---|
| 2,449,053 | 9/1948 | Burns . | |
| 2,738,669 | 3/1956 | Silverman . | |
| 3,486,366 | 12/1969 | Jackson . | |
| 3,580,051 | 5/1971 | Blevins . | |
| 4,146,025 | 3/1979 | Warncke . | |
| 4,590,793 | 5/1986 | Staats | 73/40 |

*Primary Examiner*—Kyle L. Howell
*Assistant Examiner*—Angela D. Sykes
*Attorney, Agent, or Firm*—J. Michael McClanahan

[57] ABSTRACT

Method and apparatus for determining a face respirator fit for a particular respirator on a particular person wherein after first placing the respirator on the person's face, the air interiorly to the facepiece is partially evacuated while the subject holds his breath and clamps off his nostrils, the air which then leaks into the facepiece through leakage paths between the facepiece and the wearer's face is measured by a mass flow meter in line with a vacuum source which maintains a constant negative pressure interiorly to the facepiece, the test being accomplished over a relatively short period of time. The apparatus of the invention includes modifying the respirator by sealing off the normal inspiratory openings, i.e., the inhalation filters, and in their places having ports which connect to the mass flow meter and a pressure monitoring transducer. The mass flow meter is then connected with the source of vacuum wherein the pressure transducer, after an initial negative pressure is introduced interiorly to the facepiece, maintains that negative pressure by opening and closing a valve connected with the vacuum source. Leakage air into the facepiece is constantly withdrawn through the mass flow meter and thus the measurement of the leaking air is indicative of the quality of air tightness sealing of the respirator to the face of the wearer.

19 Claims, 1 Drawing Sheet

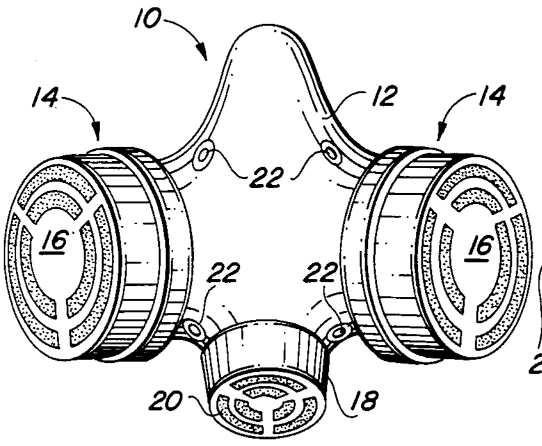
FIG. 1
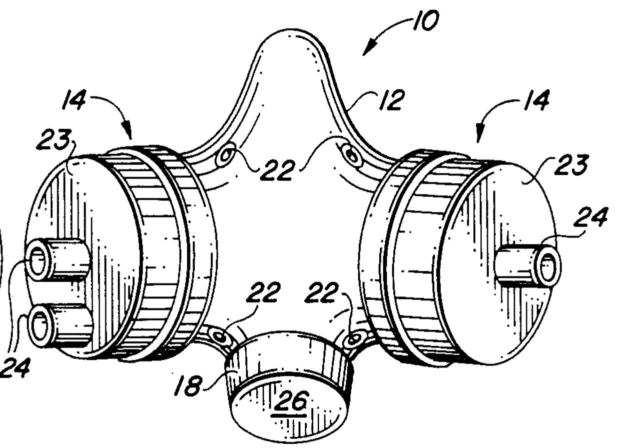
FIG. 2
FIG. 3
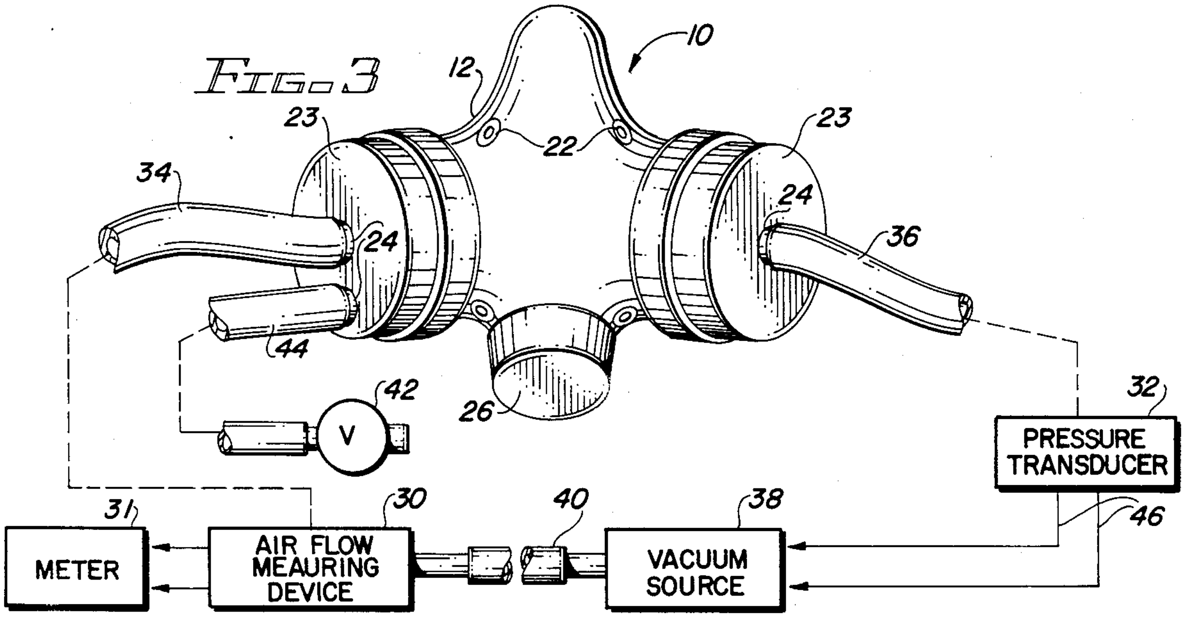
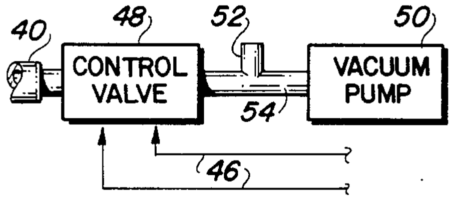
FIG. 4
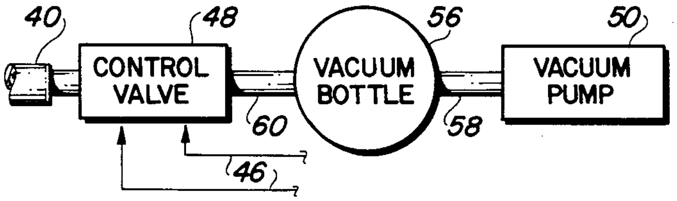
FIG. 5
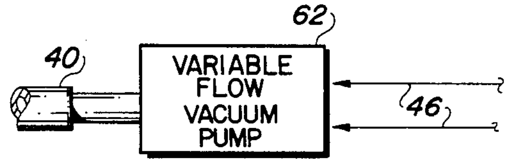
FIG. 6

METHOD AND APPARATUS FOR DETERMINING RESPIRATOR FACE MASK FIT

BACKGROUND OF THE INVENTION

1. Field of the Invention

The field of the invention is respiratory face masks, methods and apparatus for determining air tight fit of the mask to the face of the wearer.

2. Description of the Related Art

Respirators, also occasionally referred to as face masks or gas masks, are used to protect personnel from breathing in contaminants while exposed to a contaminated environment. Respirators fall into two basic classes, the first class being a supplied air respirator in which a flexible hose connects a supply of clean air to the respirator, and the second class where the respirator draws air from a surrounding contaminated environment. The latter class is the most widely used of all respirators and respirators of this class generally are constructed to cover the wearer's nose and mouth with a flexible rubber mask which is held in place with an air tight relationship to the face as much as possible through the use of one or more elastic holding straps which encircle the wearer's head.

Respirators, in the most part, are constructed of various elements comprising firstly a facepiece which may be constructed of rubber or silicone rubber and is that part which covers the nose and mouth of the wearer. The facepiece, which is differently sized and formed to fit the face, is held in place by means of the aforementioned rubber or elastic head bands which attach, by means of snaps, to the facepiece and surrounds the head in one or more loops.

In the usual respirator of the second class, three apertures are formed in the facepiece, two on opposite sides and one in the lower center area. The two apertures on opposite sides are designed to receive the inhalation filter cartridges which are the means by which contaminants are filtered from the environmental air and provides the path for air pulled into the facepiece by the negative pressure created interiorly by the person inhaling. These inhalation filter cartridges, which appear to be extensions of the wearer's cheeks, are built-up devices having cartridge adaptors, inhalation valve flaps, filters of different types, perforated filter covers, gaskets, and the like. In addition, innerchangeable cartridges are available which combine the filter and filter cover into a single cartridge which is screwed on to threads formed on the cartridge adaptor. The cartridge adaptor is in an air-sealed relationship to the facepiece. In the lower center portion of the facepiece is the exhalation valve which opens during the time the wearer is exhaling, i.e., when there is an over-pressure interiorly to the facepiece relative to the environment, and the exhalation valve closes when the wearer inhales, i.e., there is a negative pressure interiorly to the facepiece relative to the environment. In addition, it is common also to place oppositely operating, but similar type valves in the inhalation filter cartridges, i.e., upon an over pressure interiorly to the facepiece, the valve closes.

By innerchange of different types of filter elements, a respirator may be specifically designed for a particular environment. For example, activated charcoal acts as a scrubber for gases whereas felt, cloth, or paper may be utilized in a paint aerosol environment.

As can well be imagined, of primary concern is the fit of the respirator against the face of the wearer insomuch much as if there is not an air tight fit, the environment will be drawn into the face mask between the wearer's face and the respirator upon inhalation, and thus the purpose of the respirator is defeated or at least in part. Various tests and methods have been devised to determine a "fit factor" for a respirator as applied to a certain person and the way the test is designed, the higher the number the better the fit. Thus, the fit factor is a ratio of the contamination level outside the mask divided by the contamination level inside the mask; or alternatively the ratio of total (purified+contaminated) air inspired divided by contaminated air inspired. For example, if a person breathes in air at a rate of 35 liters/-minute and it has been determined that 350 milliliters/-minute did not enter through the purifying inhalation filter cartridges, the fit factor is a ratio of 35 l./minute÷0.35 l./minute=100.

The most common method used today of determining fit factor for respirators is to place a person in an environment with a known concentration of contamination, collect air from the mask interior, and then determine the concentration of the contaminant in such collected air. Air borne contaminants which are commonly used in tests of these types are di-octal phthalate, commonly called DOP, corn oil, and sodium chloride salt fogs. The techniques by which monodispersed contaminant particles are precisely generated and uniformly dispersed in air for these tests are generally rather complicated.

Another major problem in evaluating respirators through today's methods is the method by which the concentration of the air borne contaminant, more commonly called aerosols, is measured. One of the most popular methods used today is to measure concentration through light scattering techniques, i.e., shining a light through a known volume of the captured contaminants and then determining through photometric cells and light scattered which is related then to concentration. However, this method has problems as in many cases, the measuring equipment lies some distance away from the party under test (usually ouside a sealed chamber) and hoses used to convey the breathed air with contaminants may be porous or partially porous to the particular contaminant or may adsorb the contaminant.

As may well be imagined, since wearer's faces are differently shaped and sized, obviously one respirator is not going to fit all people. Accordingly, the companies manufacture different sizes. Nevertheless, from the very fact that there are different sized available in most respirators, attempts to fit the respirator to one particular person means that there is still a compromise. In addition, the rate of contaminant leakage changes as the wearer breathes at different rates and volumes because of different work rates. The fit factor determined for a wearer in a resting condition may not adequately describe the fit factor achieved with the same respirator under more vigorous work conditions.

Consequently, missing from the field of respirator fit data is how well respirators fit a person and what degree of protection is afforded a wearer who wears the mask over a long period of time and under varying conditions of work.

During inhalation, or as more commonly called in the field, "inspiration", the inspiratory volume and the inspiratory flow rate, i.e., the rate of movement of air into the wearer's lungs, causes a negative pressure difference between the environment outside the mask, and the interior of the face mask. Increasing inspiratory volume and increasing inspiratory flow rate causes a greater negative pressure to be induced inside the mask during more rigorous work conditions. The varying of negative pressure interiorly to a mask simulates varying conditions of work of the wearer, and thus provides a method for determination of fit factor under the varing conditions.

In addition, because of the time, expense, and difficulty in determining fit factor for a person of a particular respirator, many workers who wear respirators day in and day out are never checked to see which respirator, of all available respirators, achieves for them the highest, and thus the safest, fit factor in order that maximum protection may be afforded.

Accordingly, it is apparent that there exists a need for method and apparatus by which the fit factor for any one mask upon an individual's face may be determined, and determined under conditions which the wearer may expect to encounter during his work day.

SUMMARY OF THE INVENTION

This invention relates to method and apparatus for determining the fit of a particular respirator to a specified person or wearer under conditions and in environments which the wearer is expected to encounter during the work day. Since, as previously discussed, contaminants are drawn into the respirator through leakage paths between the face of the wearer and the respirator during the periods of inspiration, i.e., inhalation when a negative pressure is created within the respirator, and since during times when a wearer is actively working and demanding more breath, a greater negative pressure is created, pressure monitoring of various negative pressures interiorly to the respirator and measurement of the rate at which air is removed in order to sustain the negative pressure can be a means of determining the best fit under all conditions.

Firstly, the interior parts of the two inhalation filter cartridges which attach to the facepiece are removed, as well as the perforated filter cover, and non-perforated filter covers are screwed on to the cartridge adaptor attached to the facepiece. Through these filter covers are place cylindrical ports which communicate with the facepiece interior and to which are attached rubber or plastic tubing. The valve cover of the exhalation valve, which was perforated as original equipment, is removed and a nonperforated valve cover substituted so that no air will pass through the exhalation valve under any circumstances.

In the preferred embodiment, three ports penetrate the total of the non-perforated inhalation filter covers for connection to the apparatus of the invention. For convenience, two ports may be situated in one filter cover and one in the other. Firstly, to one port located through an inhalation filter cover, a short rubber tube is attached which has a quick close air valve attached at the opposite end, thereby forming a breathing port. Then, to another port penetrating one of the inhalation filter covers is attached a pressure monitor transducer of the type that emits an electrical control signal linearly indicative of the sensed air pressure difference from a pre-set desired air pressure. Through the other port in the inhalation filter cover is connected flexible tubing which in turn connects to the inlet of a mass flow meter. To the outlet of the mass flow meter is also connected a source of vacuum pressure. This source of vacuum pressure comprises a vacuum pump with an electrically controlled air valve interposed in the flexible tubing between the mass flow meter and the vacuum pump. The electrically controlled air valve is connected to the electrical output of the pressure monitoring transducer.

In operation, the facepiece is first fitted on the wearer with the fitting straps all attached to make the mask as air tight as possible, yet be comfortable. The flexible tubing is connected to the ports in the inhalation filter covers as above noted. The party breathes through the breathing port prior to the commencement of the test. Next, the apparatus is set in operation which includes starting the vacuum pump. The pressure transducer senses that the pressure interiorly to the facepiece is not the negative pressure valve pre-selected and a signal is sent to the electrically controlled air valve interposed between the facepiece and the vacuum pump. The air valve opens and the vacuum pump pulls air through the mass flow meter and the electrically controlled air valve. Since the capacity of the vacuum pump utilized in the test is small relative to the amount of air which a person may pull through the breathing port, sufficient air is available for breathing simultaneously with the vacuum pump running. The subject party is then instructed to partially exhale his lungs of air, close his mouth, and to hold his breath. Then, the air valve at the end of the breathing port is closed off, sealing the mask from all entrance of outside air other than through any leakage paths that may exist or develop. As the negative pressure interiorly to the facepiece apparoaches the preselected level to which the pressure monitor transducer is set, the proportional signal outputted by the pressure monitor transducer is reduced which in turn reduces the size of the orifice in the electrically controlled air valve until the steady-state pre-selected negative pressure has been established in the respirator interior. A period of 3 to 5 seconds is permitted to allow the negative pressure to reach a steady state equilibrium throughout the interior of the facepiece, the equipment, and the tubing.

The ideal situation would be that very little air leaks interiorly to the facepiece and thus the electrical voltage output of the pressure monitor transducer would be zero with perhaps a small output from time to time indicating that there was some small amount of leakage, and as the pressure interiorly to the mask rose, the pressure monitor transducer would detect it. Correspondingly, the electrically controlled air valve would be closed the majority of the time and then opened as it received an electrical signal from the pressure monitor transducer to thereby permit the vacuum pump to regain the negative pressure desired. Thus the system would be indicative of the average of leakage air over an extended period of time.

However, in reality, test indicate that there is a constant leakage of environmental air into the facepiece such that the pressure monitor transducer is constantly outputting a signal and correspondingly, the electrically controlled air valve is never completely closed off and air is constantly being pulled through the mass flow meter.

Accordingly, the electrical signal from the pressure monitor transducer continues to control the opening of the electrically controlled air valve so that the negative pressure in the facepiece is maintained at its pre-selected level. Selection of this pressure is made to replicate the negative pressure normally generated in the mask during inspiration through the air purifying cartridges which duplicates the negative pressure driving force for air leakage into the mask.

The flow rate of air removed from the facepiece through the mass flow meter by the vacuum system which was required to maintain the pre-selected negative pressure is equal to the leakage flow rate of air into the respirator. Thus, measurement of the flow rate of the removed air utilizing the mass flow meter gives an absolute determination of leakage around the facepiece for the particular negative pressure induced interiorly to the facepiece. Obviously, the negative pressure interiorly to the facepiece can be increased (made more negative) thereby simulating a wearer working hard and thus demanding more air. Under such varying conditions, the leakage air flow can be determined and the fit factor over the expected simulated conditions determined for one wearer with different respirators. Thus the best respirator for any particular person may be easily determined.

In the preferred embodiment of the invention, the vacuum source was a constant flow vacuum pump connected to the electrically operated air valve wherein, while the pump was running full time, a bypass valve was inserted in the flexible tubing between the electrically controlled air valve and the vacuum pump in order that the vacuum pump may be pumping air at a constant rate while air flows through the electrical control valve at a variable rate. An alternate embodiment of the vacuum source comprised a variable flow vacuum pump which was directly controlled by the output of the pressure transducer monitor wherein the pump flow rate was adjusted by the pressure transducer signal to maintain the pre-selected negative pressure in the mask during the test. In the latter case, an electrically controlled air valve was not necessary since the variable flow vacuum pump pulls air directly through the mass flow meter.

It is an object of the subject invention to provide a means for determining the fit factor of any one mask upon any wearer's face in an expedient and safe manner without exposing the wearer to a contaminated environment.

It is further an object of the subject invention to provide a means for a party who works in a contaminated environment to select the best respirator or mask for his use.

It is still further an object of the subject invention to provide a method and apparatus for determining the leakage into a respirator or mask that comes via leakage paths between the respirator and the wearer's face.

Other objects of the invention will in part be obvious and will in part appear hereinafter. The invention accordingly comprises the apparatus comprising the construction, combination of elements, and arrangement of parts, together with the method of operating the same which are exemplified in the following detailed disclosure and the scope of the Application which will be indicated in the Claims.

BRIEF DESCRIPTION OF THE DRAWINGS

For further understanding of the nature and object of the present invention, reference should be had to the following detailed description taken in connection with the accompanying drawings wherein:

FIG. 1 is a front view of a typical respirator;

FIG. 2 is a front view of a respirator modified for use in the subject invention;

FIG. 3 is a block schematic diagram of the subject invention;

FIG. 4 is an embodiment of the vacuum source;

FIG. 5 is an alternate embodiment of the vacuum source; and

FIG. 6 is another alternate embodiment of the vacuum source.

In various views, like index numbers refer to like elements.

DETAILED DESCRIPTION OF THE PREFERRED EMBODIMENT

Referring now to FIG. 1, a front view of a respirator or mask 10 for wearing by a party and which covers the party's nose and mouth, is illustrated. Firstly, the facepiece 12 is constructed of soft pliable rubber or silicone adapted to insure, as far as possible, an air tight seal betweem itself and the wearer's face. In many respirators, there is an oversized lip around the edge which resides next to the face to insure the best fit possible. Other respirators or masks not illustrated may be expanded in size and scope to cover the full face, including the eyes. On both sides of facepiece 12 are the inhalation filter cartridges 14 through which the environmental air passes, and is filtered for breathing by the wearer. These inhalation filter cartridges 14 comprise various parts consisting of a perforated filter cover 16 which is generally cup-shaped, much like the lid on a jar, and has female threads around its rim adapted to engage male threads on the base cartridge adaptor. The interior of inhalation filter cartridge 14 is packed with various types of filters such as cloth, felt, activated charcoal filled pads and the like. In addition, a butterfly type popper valve may be situated interiorly to the cartridge adaptor which opens upon inhalation (when negative pressure relative to the environment air pressure is generated) and closes upon exhalation (when over pressure relative to the environment air pressure is generated). Lastly, the inhalation filter cartridge 14 mates with the facepiece 12 by its cartridge adaptor engaging in an air-tight sealed manner with an opening in the facepiece 12.

At the lower center portion of facepiece 12 is the exhalation valve 18 which is simply a butterfly type popper valve flap adapted to open during times of overpressure interiorly to the facepiece, i.e., exhalation by the wearer. and to close during periods of negative pressure interiorly to the facepiece, i.e., inhalation. The exhalation valve similarly is capped with a perforated exhalation valve cover 20 which, like the inhalation filter cover, is cup-shaped, much like a jar lid and snaps on to the exhalation valve seat. Also, like the inhalation filter cartridge, the exhalation valve 18 mates with an opening through the facepiece 12 in an air-tight type arrangement.

Lastly, shown on respirator 10 are the snaps 22 by which the straps (not shown) attach to wrap around the wearer's head in order to hold the facepiece 12 against the wearer's head.

FIG. 2 illustrates the subject respirator 10 with modifications wherein the inhalation filter cartridges 14 of FIG. 1 have had all their interior parts removed, i.e., filter meduim and valve flaps, together with perforated filter covers 16 removed and replaced with air-right, non-perforated inhalation filter covers 23 where short cylindrical ports 24 have been attached by soldering or other mechanical air tight connection methods. This provides an unobstructed air path through the ports into the now hollow inhalation filter cartridge 14 to the interior of facepiece 12. It is noted that ports may be located on either or both of the non-perforated inhalation filter covers 23, all providing air access from the environment to the interior of facepiece 12.

With respect to the exhalation valve 18, the perforated exhalation valve cover 20 has been removed and replaced with a non-perforated exhalation valve cover 26 in order to assure that the exhalation valve is not a source of leakage during the test. The removal and replacement of the perforated exhalation valve cover 20 may or may not require the removal of the butterfly type popper valve flap interiorly to the exhalation valve 18, depending upon each type of respirator's construction. Regardless of whether the butterfly type popper valve flap is left interiorly to the exhalation valve 18, the valve is sealed off from possible air passage.

While it has been noted that the inhalation filter covers have been utilized to receive the air ports 24, and that of the three ports needed, two have been placed on one inhalation filter cover, any arrangement could be utilized for placement of these three ports among the three total covers. The sole purpose is to permit, through the breathing ports, unobstructed air access into the interior of the facepiece without modifying the configuration of the facepiece fit.

By modifying the respirator 10 as shown in FIG. 1 to the configuration shown in FIG. 2, the test to determine the fit factor of any mask on any wearer may proceed, together of course, with the equipment which will be detailed supra.

Referring now to FIG. 3, a schematic block diagram of the respirator and other apparatus necessary for the invention is shown. Firstly, respirator 10, and more particularly facepiece 12, is operably attached via the modified inhalation filter covers 23 and their respective cylindrical ports 24 to the air-flow metering device 30 and the pressure transducer 32 by flexible tubing 34 and 36, respectively. Situated between the air-flow measuring device 30 and pressure transducer 32 is the source of vacuum 38 which is attached to air-flow measuring device 30 by means of flexible tubing 40 to provide an air passageway to utilize this vacuum source. Electrical connections 46 connecting pressure transducer 32 to the vacuum source 38 is also shown. Next, operably attached to the second of the ports 24 on inhalation filter cover 23 is air valve 42, the connection being made through the means of flexible tubing 44. This becomes the breathing port. Lastly, meter 31 records the analog voltage output of air flow measuring device 30.

The function of each of the blocks shown in the schematic block diagram of FIG. 3 is as follows. The air-flow measuring device 30 comprises a means by which the passage of air is measured and recorded either by volume or by mass. In the preferred embodiment, a mass flow meter capable of measuring the mass of the air flowing over a period of time is utilized. It is intended that since the air-flow measuring device 30 will measure the mass of the air leaked into the interior of the facepiece 12 to which it directly communicates, this device must be very accurate and capable of measuring extremely small mass flow rates of air. The vacuum source 38, which pulls, by means of a partial vacuum, the air from the interior of facepiece 12 through the air-flow measuring device 30 is directly coupled to the air-flow measuring device 30 in order that the air path be continuous from the vacuum source through the tubing connecting the air-flow measuring device into the interior of facepiece 12.

As air leaks past the wearer's face and facepiece 12 into the interior of the repsirator 10, vacuum source 38, being operated to maintain a constant negative pressure interiorly to facepiece 12, will pull an equal volume of air through the air-flow measuring device as leaks into the respirator. By this means, measuring the mass of the air which flows through the air-flow measuring device 30 is a measurement of the leakage into the respirator from the environment. Measurements are thus recorded on voltage meter 31.

The only part remaining to be described is the means by which the negative pressure interiorly to facepiece 12 is sensed in order to maintain a constant fixed negative pressure. This is accomplished by a means of pressure monitor transducer 32 connected by flexible tubing through port 24 to facepiece 12. The electrical signal output of the pressure transducer 32 is indicative of a change in air pressure from a present amount and is sent to the vacuum source 38 by means of electrical lead lines 46. In this manner, the vacuum source can be controlled so that a vacuum is applied to the system to intitiate the start of the test by establishing the desired negative pressure interiorly to the facepiece and connective tubing and instruments, and during the test to maintain the negative air pressure interiorly to the facepiece and connective tubing and instruments at the pre-selected value. As pressure monitor transducer 32 senses that the pressure interiorly to the facepiece 12 is approaching the pre-selected level, it responds by reducing the voltage of the signal on the electrical lead lines 46 and thereby adjusts the vacuum source 30 to establish the pre-selected negative pressure in the mask interior. The air pressure monitor transducer 32 continues to seek the negative pressure desired and thereby maintains the preselected negative pressure as closely as possible. The air-flow rate to the vacuum source required to maintain the pre-selected negative pressure is measured by the air-flow measuring device 30 as described above. It is most likely that throughout the test, the vacuum source will constantly be pulling a small amount of air through the air-flow measuring device.

Now, since it is necessary for the person under test to breathe for the period of time prior to starting of the test, apparatus connected to port 24 on the modified inhalation filter cover 23 allows pre-test breathing. Air valve 42 connects with the cylindrical breathing port 24 of the inhalation filter cover 23 through means of flexible tubing 44. With air valve 42 open, the subject may breathe through the breathing port 24 until the test begins.

When the test commences, the subject is instructed to exhale most of the air from his lungs, to close his mouth, and to hold his breath. Then air valve 42 is closed. If the subject is unable to positively close off his nose to air flow from the respiratory system while holding his breath, a nose clamp may be worn prior to and during the test. Then, the vacuum source 38 is utilized to create a chosen negative pressure (negative with respect to the environment, but still an absolute pressure value) interiorly to facepiece 12 until the pressure transducer 32 indicates that the desired pressure is reached. This will take a few seconds. After the air pressure has been set and stabilized interiorly to the facepiece 12, the mass flow rate of air which leaks into the respirator is measured by the mass flow meter 30 over a set period of time by the testing operator monitoring its output. It may be expedient to insert air chambers and/or dampers in the flexible tubing between different pieces of the apparatus of the invention to rapidly reach the steady state pressure and/or to provide a smooth, non-pulsed vacuum source.

In the preferred emodiment, an Omega brand high performance mass flow meter of the FMA-200 Series was utilized as the air-flow measuring device 30 shown in FIG. 3. Similarily, an Omega amplified voltage output type pressure transducer 160 Series was utilized as the pressure transducer 32. Both the mass flow meter and the pressure transducer outputted their respective readings by electrical lead lines, the lead lines from the pressure transducer as shown in FIG. 3 directed to the vacuum source. The lead lines from the mass flow meter are monitored by the operator administering the fit factor test wherein the analog electrical voltage output read on meter 31 is indicative of the mass of the air passing through the mass flow meter over the period of the test. If the operator is more familar with the volume of air measured, knowing the mass of the air flowing, pressure, and temperature, the volume can be calculated. The air valve 42 shown in FIG. 3 is of conventional type and may be hand operated and is readily available and well known in the art.

The vacuum source 38 may take any one of a number of forms. In the preferred embodiment of the invention, the arrangement shown in FIG. 4 was utilized. Here, the vacuum source 38 comprised a continuously running vacuum pump 50 which was connected to an electrically controlled control valve 48 whose electrical controls were supplied by electrical leads 46 from pressure transducer 32 as shown in FIG. 3. The control valve 48 then was connected to the air-flow measuring device 30 by the same flexible tubing 40 as shown in FIG. 3. Since vacuum pump 50 was a continuous vacuum pump, air bleed 52 was provided connected to tubing 54 in order that some air would be pulled into the vacuum pump at all times, even when the conrol valve 48 was closed. In the preferred embodiment, a Brooks Mass Flow Control Valve, Model 5836, which is a proportional control valve, was utilized and vacuum pump 50 was a Dayton Speedaire diaphram-type vacuum pump. Meter 31 is a high input impedance volt meter of which many abound.

An alternate embodiment of vacuum source 38 is shown in FIG. 5. Here, much of the same componenets as shown in FIG. 4 are utilized, namely the flexible tubing 40 to the air-flow measuring device, the control valve 48 controlled by electrical lead line 46 from pressure transducer 32, and the vacuum pump 50. The only difference has been the addition of the vacuum bottle 56 which pulls air through the control valve 48 as the proportional control valve 48 is opened. Vacuum pump 50 does not run continuously, but is initiated prior to the commencement of the fitting test and only for the purpose of evacuating vacuum bottle 56. Once a suitable partial vacuum has been established in vacuum bottle 56, pump 50 is then shut off and then the test operated with vacuum bottle 56 providing the source of vacuum. Connecting vacuum bottle 56 to the vacuum pump 50 is air tubing 58, while tubing 60 connects vacuum source 56 to the control valve 48.

The last remaining alternate embodiment for vacuum source 38 is shown in FIG. 6 wherein the block referred to as Numeral 62 is a variable flow vacuum pump whose operation is controlled by means of electrical leads 46 from pressure transducer 32 shown in FIG. 3. The output of the variable flow vacuum pump 62 is directed into the same flexible tubing 40 which connects with the air-flow measuring device 30 as shown in FIG. 3.

Another alternate embodiment of the air-flow measuring device 30 as shown in FIG. 3 which may be utilized is an orifice flow meter, rather than the mass flow meter earlier referred to of a type commonly available. The orifice flow meter outputs a signal that is a linear function of the differential pressure that is created across the orifice as air flows through it. Meters of these types are commonly available.

Empirical data which is widely available indicates accepted values for inspiration flow rates for various sized persons performing activites while wearing a respirator, such activities comprising sitting, walking, and various types of labor. Similarly, the negative pressure interiorly to the facepiece for these different inspiratory flow rates is also known through empirically obtained data. Thus, the negative pressure in the facepiece can be adjusted to these known negative pressures, and the leakage flow rate, as determined by the air-flow measuring device, related to the empirical data and then the ratio of the inspiratory flow rate over the leakage flow rate determines the fit factor for a particular respirator applied to a particular person and for a preselected negative pressure.

As is also obvious, the average volume of air inspired by a person through respirators doing various tasks are also known from comparably obtained data and, at any pressure, and knowing the mass flow over a set period of time, the volume of the air may easily be calculated and therefore the same fit factor may be determined by the ratio of the volume of the inspired air to the volume of the leakage air.

It is apparent from the above discussion that determining the fit factor for any one party with a particular respirator can be done in just a few seconds, not more than ten or fifteen seconds, for each pre-selected negative pressure desired to be present interiorly to the facepiece. Further, it is not necessary for the party to be placed in a contaminated environment. Consequently, in just a matter of moments, the best fitting respirator for any particular person can be determined for the range of activities the party is expected to be doing in a contaminated environment.

It is also apparent from the above discussion that the method and apparatus embodied in this specification may also be applied to respirators that have no separate inhalation and exhalation cartridges and/or ports, or where a single air line leads to the respirator facepiece since in accordance with the method described, all inhalation and exhalation cartridges and/or ports are air-sealed and at least one air-port added in order to provide communication between the interior of the respirator facepiece and the equipment utilized in the method to determine the respirator fit factor.

While a preferred embodiment and alternate embodiments of the apparatus have been shown and described, together with the method of determining respirator fit factor, it will be understood that there is no intent to limit the invention by such disclosure, but rather it is intended to cover all modifications of the apparatus and method, and alternate constructions, falling within the spirit and the scope of the invention as defined in the appended Claims.

I claim:

1. A method for determining face respirator fit by measurement of leakage air into the interior of the respirator entering between the respirator and the person's face comprising the steps of:

sealing the sources of inhalation and exhalation air entrance into and out of the respirator;

placing the respirator upon the face of the person;

having the person expel air from their lungs and hold their breath;

evacuating air interiorly to the respirator until a desired partial vacuum air pressure is achieved;

monitoring the pressure interiorly to the respirator;

withdrawing air from the respirator to maintain constant the desired partial vacuum air pressure interiorly to the respirator;

measuring the air withdrawn from the respirator whereby knowing the air withdrawn to maintain the constant partial vacuum air pressure, the leakage air is known and the fit of a respirator on a person determined.

2. The method of determining face respirator fit as defined in claim 1 wherein the step of sealing the sources of inhalation and exhalation air entrance into and out of the respirator comprises the step of sealing the inhalation and exhalation filter cartridges.

3. The method of determining face respirator fit as defined in claim 1 wherein the step of evacuating air interiorly to the respirator comprises the step of operably connecting the respirator to a source of partial vacuum whereby the vacuum may be utilized to withdraw air from the interior of the respirator.

4. The method of determining face respirator fit as defined in claim 3 wherein the step of operably attaching the respirator to a source of partial vacuum includes the step of installing an air passage port through the respirator, and attaching an air hose between the port and the source of partial vacuum whereby the source of partial vacuum communicates with the interior of the respirator to thereby withdraw air from the interior of the respirator.

5. The method of determining face respirator fit as defined in claim 1 wherein the step of monitoring the pressure interiorly to the respirator comprises the steps of installing an air passage port through the respirator, attaching an air hose between the port and an air pressure transducer whereby the air pressure transducer communicates with the interior of the respirator and thereby monitors the air pressure interiorly to said respirator.

6. The method of determining face respirator fit as defined in claim 5 wherein the step of withdrawing air from the respirator to maintain constant the desired partial vacuum air pressure interiorly to the respirator comprises the step of regulating the withdrawal of air from the respirator by regulating an air flow valve interposed between the respirator and the source of partial vacuum.

7. The method of determining face respirator fit as defined in claim 6 wherein the step of regulating the air-flow valve comprises the step of outputting a signal from the air pressure transducer and utilizing the signal to operate the air flow valve.

8. The method of determining face respirator fit as defined in claim 1 wherein the step of measuring the air withdrawn from the respirator comprises the step of measuring the mass of the air withdrawn from the respirator with a mass flow meter.

9. The method of determining face respirator fit as defined in claim 8 wherein the step of measuring the air withdrawn from the respirator includes the step of metering the output of the mass flow meter with a volt meter whereby the volt meter indicates the mass of air withdrawn and knowing the mass of the air withdrawn, the air leakage into the face respirator is known and the fit of the respirator determined.

10. Apparatus for determining face respirator fit by measurement of leakage air into the interior of the respirator entering between the respirator and the person's face comprising:

a respirator having sources of inhalation and exhalation air entrance into and out of the respirator sealed;

at least one air-port through said respirator communicating with the interior of the respirator;

a vacuum source operably connected to said air-port, said vacuum source having air passage communication with the interior of said respirator, said vacuum source adapted to withdraw air interiorly from said respirator when said respirator is fitted upon a person's face until a desired partial vacuum air pressure is achieved and to maintain constant the desired partial vacuum air pressure interiorly to the respirator as air leaks into the respirator;

an air pressure transducer operably connected to said air-port, said air pressure transducer having air passage communication with the interior of said respirator, said air pressure transducer adapted to monitor the pressure interiorly to said respirator; and an air-flow measuring device operably connected between said air-port and said vacuum source, said air-flow measuring device having air passage communication with the interior of said respirator and said vacuum source, said air-flow measuring device adapted to measure the air withdrawn from the respirator by said vacuum source whereby as said vacuum source withdraws air from the respirator to maintain constant the desired partial vacuum air pressure interiorly to the respirator, the air flow measuring device measures the air flow withdrawn from the respirator and, knowing the air flow withdrawn to maintain constant partial vacuum air pressure, the leakage air is also known, and the fit of a respirator on a person so determined.

11. The apparatus for determining face respirator fit as defined in claim 10 wherein said air pressure transducer includes an electrical signal output which varies according to the air pressure sensed, said electrical signal output operably connected to said vacuum source.

12. The apparatus for determining face respirator fit as defined in claim 11 wherein said vacuum source is adapted to receive said air pressure transducer electrical signal output and withdraw air from the interior of said respirator through said air flow measuring device responsive to said electrical signal output so received from said air pressure transducer to maintain constant the partial vacuum air pressure.

13. The apparatus for determining face respirator fit as defined in claim 12 wherein said air-flow measuring device defines a mass flow meter means for measure the mass of the air flowing therethrough between said respirator and said vacuum source.

14. The apparatus for determining face respirator fit as defined in claim 13 wherein said mass flow meter includes an electrical signal output indicative of the mass of the air flowing therethrough, and a volt meter electrically connected to said mass flow meter electrical signal output whereby the mass of the air flowing through said mass flow meter may be read upon said volt meter.

15. The apparatus for determining face respirator fit as defined in claim 14 wherein said vacuum source comprises a control valve and vacuum pump operably attached thereto, said control valve operably connected to said electrical signal output of said air pressure transducer and operably connected to said air-flow measuring device whereby said control valve regulates the flow of air withdrawn from the interior of said respirator to maintain constant the partial vacuum air pressure.

16. The apparatus for determining face respirator fit as defined in claim 14 wherein said vacuum source comprises a variable flow vacuum pump, said variable flow vacuum pump operably connected to said electrical signal output of said air pressure transducer whereby said variable flow vacuum pump is responsive to said electrical signal output of said air pressure transducer and withdraws air from the interior of said respirator.

17. The apparatus for determining face respirator fit as defined in claim 14 wherein said vacuum source comprises a control valve, a vacuum bottle operably connected to said control valve, and a vacuum pump operably connected to said control valve, said control valve operably connected to said pressure transducer whereby said vacuum pump establishes a partial vacuum in said vacuum bottle and said vacuum bottle withdraws air from said respirator through said air-flow measuring device.

18. The apparatus for determining face respirator fit as defined in claim 10 wherein said vacuum source operably connected to said air-port defines said vacuum source connected to said air-port by an air hose; said air pressure transducer operably connected to said air-port defines said air pressure transducer connected to said air-port by an air hose; and said air-flow measuring device operably connected between said air-port and said vacuum source defines said air-flow measuring device connected between said air-port and said vacuum source by a pair of air hoses.

19. The apparatus for determining face respirator fit as defined in claim 10 further comprising a plurality of air-ports through said respirator communicating with the interior of the respirator, one of said plurality of air-ports operably connecting said vacuum source, a second of said plurality of air-ports operably connecting to said air pressure transducer, and a third of said plurality of air-ports connecting said air-flow measuring device.

* * * * *